United States Patent [19]

Burjes et al.

[11] Patent Number: 4,997,968
[45] Date of Patent: Mar. 5, 1991

[54] METHOD OF PREPARING MONOTHIOPHOSPHORIC ACID BY SULFURIZING A PHOSPHITE IN THE PRESENCE OF AN AMIDE

[75] Inventors: Louis Burjes, Wickliffe; Alan C. Clark, Mentor, both of Ohio

[73] Assignee: The Lubrizol Corporation, Wickliffe, Ohio

[21] Appl. No.: 413,897

[22] Filed: Sep. 28, 1989

[51] Int. Cl.$^5$ ............................................. C10M 135/02
[52] U.S. Cl. ................................ 558/120; 252/32.7 E; 558/131
[58] Field of Search .................. 423/303; 558/87, 131, 558/132, 120

[56] References Cited

U.S. PATENT DOCUMENTS 4,369,147  1/1983  Michalski .............................. 558/87
4,470,933  9/1984  Michalski .............................. 558/87

Primary Examiner—Jacqueline V. Howard
Attorney, Agent, or Firm—Joseph P. Fischer; Frederick D. Hunter; James L. Cordek

[57] ABSTRACT

A method of preparing an oil-soluble composition is disclosed. The method comprises preparing a dihydrocarbyl monothiophosphoric acid characterized by the formula

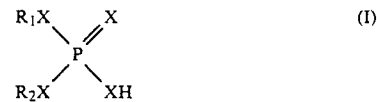

(I)

wherein $R_1$ and $R_2$ are each independently hydrocarbyl groups of from 1 to about 30 carbon atoms and X is oxygen or sulfur, with the proviso that one X is sulfur comprising reacting
  (A) a phosphite ester of the structure

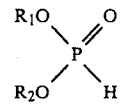

with
  (B) a sulfur source, in the presence of
  (C) a catalytic amount of an amide of the structure $R_3CONR_4R_5$ wherein $R_3$, $R_4$ and $R_5$ are each independently hydrogen or a hydrocarbyl group containing from 1 to about 30 carbon atoms or an ethoxylated amide of the structure

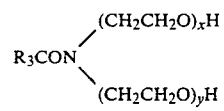

wherein the sum of x and y is from 1 to about 50; and isolating the reaction product obtained.

19 Claims, No Drawings

METHOD OF PREPARING MONOTHIOPHOSPHORIC ACID BY SULFURIZING A PHOSPHITE IN THE PRESENCE OF AN AMIDE

BACKGROUND OF THE INVENTION

1. Field of the Invention

This invention relates to the preparation of oil-soluble dihydrocarbyl monothiophosphoric acid compositions, and the use of such compositions in lubricants, fuels and greases.

2. Description of the Related Art

U.S. Pat. No. 3,984,448 (Lippsmeier, Oct. 5, 1976) relates to a process for making metal dialkylthiophosphates of the general formula:

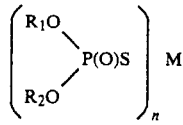

in which $R_1$ and $R_2$ stand for identical or different linear and/or branched alkyl radicals having from 1 to 6 carbon atoms, M stands for a metal cation and n indicates the valence of the metal cation concerned, wherein O,O-dialkylphosphites of the general formula

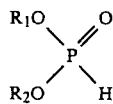

in which $R_1$ and $R_2$ have the meanings given hereinabove, are reacted with a compound yielding the metal cation M, in the presence of pulverulent sulfur and one or more organic solvents at elevated temperature.

The organic solvents are selected from alcohols, ethers, aliphatic and aromatic hydrocarbons, and chlorinated saturated or unsaturated hydrocarbons.

SUMMARY OF THE INVENTION

This invention is directed towards the preparation of oil-soluble monothiophosphoric acid compositions and to the use of such compositions in lubricants, fuels and greases. These compositions have utility as high torque extreme pressure agents. The dihydrocarbyl monothiophosphoric acid composition of the present invention is characterized by the formula

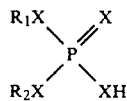

wherein $R_1$ and $R_2$ are each independently hydrocarbyl groups of from 1 to about 30 carbon atoms and X is oxygen or sulfur, with the proviso that one X is sulfur. This composition is prepared by reacting (A) a phosphite ester of the structure

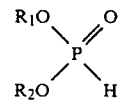

with (B) a sulfur source, in the presence of (C) a catalytic amount of an amide of the structure $R_3CONR_4R_5$ wherein $R_3$, $R_4$ and $R_5$ are each independently hydrogen or a hydrocarbyl group containing from 1 to about 30 carbon atoms or an ethoxylated amide of the structure

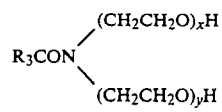

wherein the sum of x and y is from 1 to about 50.

DETAILED DESCRIPTION OF THE INVENTION

The dihydrocarbyl monothiophosphoric acid compositions of the present invention are prepared by reacting (A) a phosphite ester with (B) a sulfur source in the presence of (C) a catalytic amount of an amide.

Reactant (A) The Phosphite Ester

The phosphite esters which are included in the method of the present invention are characterized by the formula:

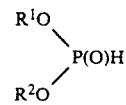

wherein $R^1$ and $R^2$ are hydrocarbyl based groups. The hydrocarbyl groups $R^1$ and $R^2$ each contain from 1 to about 30 carbon atoms; preferably from 4 to 12 carbon atoms and most preferably from 8 to 10 carbon atoms.

As used in this specification and appended claims, the terms "hydrocarbyl" or "hydrocarbon-based" denote a group having a carbon atom directly attached to the remainder of the molecule and having predominantly hydrocarbon character within the context of this invention. Such groups include the following:

(1) Hydrocarbon groups; that is, aliphatic (e.g., alkyl or alkenyl), alicyclic (e.g., cycloalkyl or cycloalkenyl), aromatic aliphatic- and alicyclic-substituted aromatic, aromatic-substituted aliphatic and alicyclic groups, and the like, as well as cyclic groups wherein the ring is completed through another portion of the molecule (that is, any two indicated substituents may together form an alicyclic group). Such groups are known to those skilled in the art. Examples include methyl, ethyl, octyl, decyl, octadecyl, cyclohexyl, phenyl, etc.

(2) Substituted hydrocarbon groups; that is, groups containing non-hydrocarbon substituents which, in the context of this invention, do not alter the predominantly hydrocarbon character of the group. Those skilled in the art will be aware of suitable substituents. Examples include halo, hydroxy, nitro, cyano, alkoxy, acyl, etc.

(3) Hetero groups; that is, groups which, while predominantly hydrocarbon in character within the context of this invention, contain atoms other than carbon in a chain or ring otherwise composed of carbon atoms. Suitable hetero atoms will be apparent to those skilled in the art and include, for example, nitrogen, oxygen and sulfur.

In general no more than about three substituents or hetero atoms, preferably no more than one, and most preferably no hetero atoms will be present for each 10 carbon atoms in the hydrocarbyl group.

Terms such as "alkyl-based group", "aryl-based group" and the like have meaning analogous to the above with respect to alkyl and aryl groups and the like.

The $R^1$ and $R^2$ groups may comprise a mixture of hydrocarbyl groups derived from commercial alcohols. Examples of some preferred monohydric alcohols and alcohol mixtures include the commercially available "Alfol" alcohols marketed by Continental Oil Corporation. Alfol 810 is a mixture containing alcohols consisting essentially of straight-chain, primary alcohols having from 8 to 10 carbon atoms. Alfol 12 is a mixture comprising mostly $C_{12}$ fatty alcohols. Alfol 1218 is a mixture of synthetic, primary, straight-chain alcohols having 12 to 18 carbon atoms. The Alfol 20+ alcohols are mostly, on an alcohol basis, $C_{20}$ alcohols as determined by GLC (gas-liquid-chromatography). The Alfol 22+ alcohols are $C_{18-28}$ primary alcohols having mostly, on an alcohol basis, $C_{22}$ alcohols. These Alfol alcohols can contain a fairly large percentage (up to 40% by weight) of paraffinic compounds which can be removed before the reaction if desired.

Another example of a commercially available alcohol is Adol 60 which comprises about 75% by weight of a straight-chain $C_{22}$ primary alcohol, about 15% of a $C_{20}$ primary alcohol and about 8% of $C_{18}$ and $C_{24}$ alcohols. Adol 320 comprises predominantly oleyl alcohol. The Adol alcohols are marketed by Ashland Chemical.

A variety of mixtures of monohydric fatty alcohols derived from naturally occurring triglycerides and ranging in chain length of from $C_8$ to $C_{18}$ are available from Procter & Gamble Company. These mixtures contain various amounts of fatty alcohols containing mainly 12, 14, 16, or 18 carbon atoms. For example, CO-1214 is a fatty alcohol mixture containing 0.5% of $C_{10}$ alcohol, 66.0% of $C_{12}$ alcohol, 26.0% of $C_{14}$ alcohol and 6.5% of $C_{16}$ alcohol.

Another group of commercially available mixtures include the "Neodol" products available from Shell Chemical Company. For example, Neodol 23 is a mixture of $C_{12}$ and $C_{15}$ alcohols; Neodol 25 is a mixture of $C_{12}$ and $C_{13}$ alcohols; Neodol 25 is a mixture of $C_{12}$ and $C_{15}$ alcohols; and Neodol 45 is a mixture of $C_{14}$ to $C_{15}$ linear alcohols. Neodol 91 is a mixture of $C_9$, $C_{10}$ and $C_{11}$ alcohols.

The dihydrocarbyl phosphites (A) useful in the present invention may be prepared by techniques well known in the art, and many dihydrocarbyl phosphites are available commercially. In one method of preparation, a lower molecular weight dialkylphosphite (e.g., dimethyl) is reacted with an alcohol or mixtures of alcohols comprising straight-chain alcohols, branched-chain alcohols or mixtures thereof. As noted above, each of the two types of alcohols may themselves comprise mixtures. Thus, the straight-chain alcohol may comprise a mixture of straight-chain alcohols and the branched-chain alcohols may comprise a mixture of branched-chain alcohols. The higher molecular weight alcohols replace the methyl groups (analogous to classic transesterification) with the formation of methanol which is stripped from the reaction mixture.

In another embodiment, the branched chain hydrocarbyl group can be introduced into a dialkylphosphite by reacting a low molecular weight dialkylphosphite such as dimethylphosphite with a more sterically hindered branched-chain alcohol such as neopentyl alcohol (2,2-dimethyl-1-propanol). In this reaction, one of the methyl groups is replaced by a neopentyl group, and, apparently because of the size of the neopentyl group, the second methyl group is not displaced by the neopentyl alcohol. Another neo alcohol having utility in this invention is 2,2,4-trimethyl-1-pentanol.

The following examples illustrate the preparation of the phosphite esters (A) which are useful in the compositions of the present invention. Unless otherwise indicated in the following examples and elsewhere in the specification and claims, all parts and percentages are by weight, and all temperatures are in degrees Celsius.

EXAMPLE A-1

A mixture of 911.4 parts (7 moles) of 2-ethylhexanol, 1022 parts (7 moles) of Alfol 8-10, and 777.7 parts (7 moles) of dimethylphosphite is prepared and heated to 125° C. while sparging with nitrogen and removing methanol as a distillate. After about 6 hours, the mixture is heated to 145° C. and maintained at this temperature for an additional 6 hours whereupon 406 parts of distillate are recovered. The residue is filtered through a filter aid and the filtrate is the desired mixed dialkyl hydrogen phosphite containing 9.6% phosphorus (theory, 9.7%).

EXAMPLE A-2

A mixture of 468.7 parts (3.6 moles) of 2-ethylhexanol, 1050.8 parts (7.20 moles) of Alfol 8-10, and 600 parts (5.4 moles) of dimethylphosphite is prepared and heated to 135° C. while purging with nitrogen. The mixture is heated slowly to 145° C. and maintained at this temperature for about 6 hours whereupon a total of 183.4 parts of distillate are recovered. The residue is vacuum stripped to 145° C. (10 mm. Hg.) and 146.3 parts of additional distillate are recovered. The residue is filtered through a filter aid, and the filtrate is the desired product containing 9.3% phosphorus (theory, 9.45%).

EXAMPLE A-3

A mixture of 518 parts (7 moles) of n-butanol, 911.4 parts (7 moles) of 2-ethylhexanol, and 777.7 parts (7 moles) of dimethylphosphite is prepared and heated to 120° C. while blowing with nitrogen. After about 7 hours, 322.4 parts of distillate are collected, and the material then is vacuum stripped (50 mm. Hg. at 140° C.) whereupon an additional 198.1 parts of distillate are recovered. The residue is filtered through a filter aid, and the filtrate is the desired product containing 12.9% phosphorus (theory, 12.3%).

EXAMPLE A-4

A mixture of 193 parts (2.2 moles) of 2,2-dimethyl-1-propanol and 242 parts (2.2 moles) of dimethylphosphite is prepared and heated to about 120° C. while blowing with nitrogen. A distillate is removed and collected, and the residue is vacuum stripped. The residue is filtered and the filtrate is the desired product containing 14.2% phosphorus.

EXAMPLE A-5

A mixture of 1752 parts (12 moles) of Alfol 8-10 and 660 parts (6 moles) of dimethylphosphite is heated to about 120°-130° C. while sparging with nitrogen. The mixture is held at this temperature for about 8 hours while removing methanol as it is formed. The reaction mixture is vacuum stripped to 140° C. at 30 mm. Hg. The residue is filtered at about room temperature, and the filtrate is the desired product containing 10.3% phosphorus (theory, 9.2).

Reactant (B) The Sulfur Source

The sulfur source which is utilized in the preparation of the monothiophosphoric acid compositions can be any of a variety of materials which are capable of supplying sulfur to the reaction. Examples of useful sulfur sources include elemental sulfur, sulfur halides, combinations of sulfur or sulfur oxides with hydrogen sulfide, and various sulfurized organic compounds as described below. Elemental sulfur is a readily available, useful and reactive sulfur source. The sulfur halides which are useful include sulfur monochloride, sulfur dichloride, etc. Combinations of sulfur and sulfur oxides (such as sulfur dioxide), with hydrogen sulfide are also useful sulfur sources.

The sulfurized organic compounds utilized as the sulfur source in preparing the monothiophosphoric acid compositions of the present invention may be aromatic and alkyl sulfides such as dibenzyl sulfide, dixylyl sulfide, dicetyl sulfide, diparaffin wax sulfide and polysulfide, cracked wax oleum sulfides, etc. One method of preparing the aromatic and alkyl sulfides includes the condensation of a chlorinated hydrocarbon with an inorganic sulfide whereby the chlorine atom from each of two molecules is displaced, and the free valence from each molecule is joined to a divalent sulfur atom. Generally, the reaction is conducted in the presence of elemental sulfur.

Examples of dialkenyl sulfides which are useful in the compositions of the present invention are described in U.S. Pat. No. 2,446,072. These sulfides can be prepared by interacting an olefinic hydrocarbon containing from 3 to 12 carbon atoms with elemental sulfur in the presence of zinc or a similar metal generally in the form of an acid salt. Examples of sulfides of this type include 6,6'-dithiobis(5-methyl-4-nonene), 2-butenyl monosulfide and disulfide, and 2-methyl-2-butenyl monosulfide and disulfide.

The sulfurized olefins which are useful as a sulfur source include sulfurized olefins prepared by the reaction of an olefin (preferably containing 3 to 6 carbon atoms) or a lower molecular weight polyolefin derived therefrom, with a sulfur-containing compound such as sulfur, sulfur monochloride and/or sulfur dichloride, hydrogen sulfide, etc.

The sulfurized organic compounds may be sulfurized oils which may be prepared by treating natural or synthetic oils including mineral oils, lard oil, carboxylic acid esters derived from aliphatic alcohols and fatty acids or aliphatic carboxylic acids (e.g., myristyl oleate and oleyl oleate) sperm whale oil and synthetic sperm whale oil substitutes and synthetic unsaturated esters of glycerides. Stable sulfurized mineral lubricating oils can be obtained by heating a suitable mineral lubricating oil with from about 1 to about 5% of sulfur at a temperature above about 175° C. and preferably at about 200° to about 260° C. for several hours so as to obtain a reaction product which is substantially non-corrosive to copper. The mineral lubricating oils sulfurized in this manner may be distillate or residual oils obtained from paraffinic, naphthenic or mixed base crudes. Similarly, sulfurized fatty oils such as a sulfurized lard oil can be obtained by heating lard oil with about 10 to 15% for a time sufficient to obtain a homogenous product.

The sulfurized fatty acid esters useful as sulfur sources can be prepared by reacting sulfur, sulfur monochloride, and/or sulfur dichloride with an unsaturated fatty acid ester at elevated temperatures. Typical esters include $C_1$-$C_{20}$ alkyl esters of $C_8$-$C_{24}$ unsaturated fatty acids such as palmitoleic, oleic, ricinoleic, petroselic, vaccenic, linoleic, linolenic, oleostearic, licanic, etc. Sulfurized fatty acid esters prepared from mixed unsaturated fatty acid esters such as are obtained from animal fats and vegetable oils such as tall oil, linseed oil, olive oil, castor oil, peanut oil, rape oil, fish oil, sperm oil, etc., also are useful. Specific examples of the fatty esters which can be sulfurized include lauryl oleate, cetyl oleate, cetyl linoleate, lauryl ricinoleate, oleyl linoleate, oleyl stearate, and alkyl glycerides.

Another class of organic sulfur-containing compounds which can be used as a sulfur source compositions of the present invention includes sulfurized aliphatic esters of an olefinic monodicarboxylic acid. For example, aliphatic alcohols of from 1 to 30 carbon atoms can be used to esterify monocarboxylic acids such as acrylic acid, methacrylic acid, 2,4-pentadienic acid, etc., or fumaric acid, maleic acid, muconic acid, etc. Sulfurization of these esters is conducted with elemental sulfur, sulfur monochloride and/or sulfur dichloride.

Another class of sulfurized organic compounds are diestersulfides characterized by the following general formula

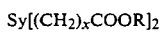

$$S_y[(CH_2)_xCOOR]_2$$

wherein x is from about 2 to about 5; y is from 1 to about 6, preferably 1 to about 3; and R is an alkyl group having from about 4 to about 20 carbon atoms. The R group may be a straight chain or branched chain group that is large enough to maintain the solubility of the compositions of the invention in oil. Typical diesters include the butyl, amyl, hexyl, heptyl, octyl, nonyl, decyl, tridecyl, myristyl, pentadecyl, cetyl, heptadecyl, stearyl, lauryl, and eicosyl diesters of thiodialkanoic acids such as propionic, butanoic, pentanoic and hexanoic acids. Of the diester sulfides, a specific example is dilauryl, 3,3'-thiodipropionate.

In one preferred embodiment, the sulfurized organic compound comprises sulfurized olefins. For example, organic polysulfides may be prepared by the sulfochlorination of olefins containing four or more carbon atoms and further treatment with inorganic higher polysulfides according to U.S. Pat. No. 2,708,199.

In one embodiment, sulfurized olefins are produced by (1) reacting sulfur monochloride with a stoichiometric excess of a low carbon atom olefin, (2) treating the resulting product with an alkali metal sulfide in the presence of free sulfur in a mole ratio of no less than 2:1 in an alcohol-water solvent, and (3) reacting that product with an inorganic base. This procedure is described in U.S. Pat. No. 3,471,404, and the disclosure of U.S. Pat. No. 3,471,404 is hereby incorporated by reference for its discussion of this procedure for preparing sulfurized olefins and the sulfurized olefins thus produced.

Generally, the olefin reactant contains from about 2 to 5 carbon atoms and examples include ethylene, propylene, butylene, isobutylene, amylene, etc. Briefly, in the first step, sulfur monochloride is reacted with from one to two moles of the olefin per mole of the sulfur monochloride, and the reaction is conducted by mixing the reactants at a temperature of from about 20° to 80° C. In the second step, the product of the first step is reacted with an alkali metal sulfide, preferably sodium sulfide, and sulfur. The mixture consists of up to about 2.2 moles of the metal sulfide per gram-atom of sulfur, and the mole ratio of alkali metal sulfide to the product of the first step is about 0.8 to about 1.2 moles of metal sulfide per mole of step (1) product. Generally, the second step is conducted in the presence of an alcohol or an alcohol-water solvent under reflux conditions. The third step of the process is the reaction between the phosphosulfurized olefin which contains from about 1 to about 3% of chlorine with an inorganic base in a water solution. Alkali metal hydroxide such as sodium hydroxide may be used. The reaction is continued until the chlorine content is reduced to below 0.5%, and this reaction is conducted at under reflux conditions for a period of from about 1 to 24 hours.

The sulfurized olefins which are useful in the compositions of the present invention also may be prepared by the reaction, under superatmospheric pressure, of olefinic compounds with a mixture of sulfur and hydrogen sulfide in the presence of a catalyst, followed by removal of low boiling materials. This procedure for preparing sulfurized compositions which are useful in the present invention is described in U.S. Pat. No. 4,191,659 the disclosure of which is hereby incorporated by reference for its description of the preparation of useful sulfurized compositions. An optional final step described in this patent is the removal of active sulfur by, for example, treatment with an alkali metal sulfide.

The olefinic compounds which may be sulfurized by this method and used as a sulfur source are diverse in nature. They contain at least one olefinic double bond, which is defined as a non-aromatic double bond; that is, one connecting two aliphatic carbon atoms. In its broadest sense, the olefin may be defined by the formula $$R^1R^2C=CR^3R^4$$

wherein each of $R^1$, $R^2$, $R^3$ and $R^4$ is hydrogen or an organic group. In general, the R groups in the above formula which are not hydrogen may be satisfied by such groups as $-C(R^5)_3$, $-COOR^5$, $-CON(R^5)_2$, $-COON(R^5)_4$, $-COOM$, $-CN$, $-X$, $-YR^5$ or $-Ar$, wherein:

each $R^5$ is independently hydrogen, alkyl, alkenyl, aryl, substituted alkyl, substituted alkenyl or substituted aryl, with the proviso that any two $R^5$ groups can be alkylene or substituted alkylene whereby a ring of up to about 12 carbon atoms is formed;

M is one equivalent of a metal cation (preferably Group I or II, e.g., sodium, potassium, barium, calcium);

X is halogen (e.g., chloro, bromo, or iodo);

Y is oxygen or divalent sulfur;

Ar is an aryl or substituted aryl group of up to about 12 carbon atoms.

Any two of $R^1$, $R^2$, $R^3$ and $R^4$ may also together form an alkylene or substituted alkylene group; i.e., the olefinic compound may be alicyclic.

The natures of the substituents in the substituted moieties described above are not normally critical and any such substituent is useful so long as it is or can be made compatible with lubricating environments and does not interfere under the contemplated reaction conditions. Thus, substituted compounds which are so unstable as to deleteriously decompose under the reaction conditions employed are not contemplated. However, certain substituents such as keto or aldehydo can desirably undergo sulfurization. The selection of suitable substituents is within the skill of the art or may be established through routine testing. Typical of such substituents include any of the above-listed moieties as well as hydroxy, amidine, amino, sulfonyl, sulfinyl, sulfonate, nitro, phosphate, phosphite, alkali metal mercapto and the like.

The olefinic compound is usually one in which each R group which is not hydrogen is independently alkyl, alkenyl or aryl, or (less often) a corresponding substituted group. Monoolefinic and diolefinic compounds, particularly the former, are preferred, and especially terminal monoolefinic hydrocarbons; that is those compounds in which $R^3$ and $R^4$ are hydrogen and $R^1$ and $R^2$ are alkyl or aryl, especially alkyl (that is, the olefin is aliphatic). Olefinic compounds having about 3 to 30 and especially about 3 to 16 (most often less than 9) carbon atoms are particularly desirable.

Isobutene, propylene and their dimers, trimers and tetramers, and mixtures thereof are especially preferred olefinic compounds. Of these compounds, isobutylene and diisobutylene are particularly desirable because of their availability and the particularly high sulfur-containing compositions which can be prepared therefrom.

Commercial sources of sulfur and hydrogen sulfide are normally used for the purpose of this sulfurization reaction, and impurities normally associated therewith may be present without adverse results. Thus, commercial diisobutene is believed to contain essentially two isomeric forms and this mixture is contemplated for use according to the present invention.

The amounts of sulfur and hydrogen sulfide per mole of olefinic compound are, respectively, about 0.3–3.0 gram-atoms and about 0.1–1.5 moles. The preferred ranges are about 0.5–2.0 gram-atoms and about 0.4–1.25 moles respectively. In batch operations, the reactants are introduced at levels to provide these ranges. In semi-continuous and continuous operations, they may be admixed at any ratio but on a mass balance basis, they are present so as to be consumed in amounts within these ratios. Thus, for example, if the reaction vessel is initially charged with sulfur alone, the olefinic compound and hydrogen sulfide are added incrementally at a rate such that the desired ratio is obtained.

The temperature range in which the sulfurization reaction is carried out is generally about 50°–350° C. The preferred range is about 100°–200° C., with about 125°–180° C. being especially suitable. The reaction is conducted under superatmospheric pressure; this may be and usually is autogenous pressure (i.e., the pressure which naturally develops during the course of the reaction) but may also be externally applied pressure. The exact pressure developed during the reaction is dependent upon such factors as the design and operation of the system, the reaction temperature, and the vapor pressure of the reactants and products and it may vary during the course of the reaction.

The method of preparing sulfurized olefins in this manner is illustrated by the following examples.

EXAMPLE S-1

Sulfur (526 parts, 16.4 moles) is charged to a jacketed, high-pressure reactor which is fitted with an agitator and internal cooling coils. Refrigerated brine is circulated through the coils to cool the reactor prior to the introduction of the gaseous reactants. After sealing the reactor, evacuating to about 2 torr and cooling, 920 parts (16.4 moles) of isobutene and 279 parts (8.2 moles) of hydrogen sulfide are charged to the reactor. The reactor is heated using steam in the external jacket, to a temperature of about 182° C. over about 1.5 hours. A maximum pressure of 1350 psig is reached at about 168° C. during this heat-up. Prior to reaching the peak reaction temperature, the pressure starts to decrease and continues to decrease steadily as the gaseous reactants are consumed. After about 10 hours at a reaction temperature of about 182° C., the pressure is 310-340 psig and the rate of pressure change is about 5-10 psig per hour. The unreacted hydrogen sulfide and isobutene are vented to a recovery system. After the pressure in the reactor has decreased to atmospheric, the sulfurized mixture is recovered as a liquid.

The mixture is blown with nitrogen at about 100° C. to remove low boiling materials including unreacted isobutene, mercaptans and monosulfides. The residue after nitrogen blowing is agitated with 5% Super Filtrol and filtered, using a diatomaceous earth filter aid. The filtrate is the desired sulfurized composition which contains 42.5% sulfur.

EXAMPLE S-2

Sulfur (151 parts) is charged to a reactor similar to the one described in EXAMPLE S-1. The sulfur is heated to 160° C. and the reactor is sealed and evacuated. Hydrogen sulfide (72 parts) is added slowly to the reactor over a period of about 4.5 hours. Thereafter, 1.6 parts of the catalyst n-butylamine are added to the reactor after about 3.8 parts of hydrogen sulfide are added. Isobutylene (157 parts) is added slowly to the reactor containing the sulfur, catalyst, and about 10 parts of hydrogen sulfide in such a manner that the rates of addition of isobutylene and hydrogen sulfide are such as to maintain 10% molar excess of hydrogen sulfide until all the hydrogen sulfide is added. The addition of the remainder of isobutylene is continued until the entire 157 parts are added. The temperature is maintained in the range of between 160°-171° C. throughout the foregoing additions and reactions with occasional cooling being necessary. The reaction is held for 5 hours at 171° C., then unreacted hydrogen sulfide and isobutene are vented to a recovery system until the pressure in the vessel is reduced to atmospheric. Separation of low boiling materials from the reaction crude is accomplished by nitrogen blowing, then vacuum stripping. The residue is then filtered. The filtrate is the desired sulfurized composition containing 47% sulfur by weight.

EXAMPLE S-3

Sulfur monochloride (2025 parts, 15.0 moles) is to 45° C. Through a sub-surface gas sparger, 1468 parts (26.2 moles of isobutylene gas) are fed into the reactor over a 5-hour period. The temperature is maintained between 45°-50° C. At the end of the sparging, the reaction mixture increases in weight of 1352 parts.

In a separate reaction vessel are added 2150 parts (16.5 moles) of 60% flake sodium sulfide, 240 parts (7.5 moles) sulfur, and a solution of 420 ml. of isopropanol in 4000 ml. of water. The contents are heated to 40° C. The adduct of the sulfur monochloride and isobutylene previously prepared is added over a three-quarter hour period while permitting the temperature to rise to 75° C. The reaction mixture is refluxed for 6 hours, and afterward the mixture is permitted to form into separate layers. The lower aqueous layer is discarded. The upper organic layer is mixed with two liters of 10% aqueous sodium hydroxide, and the mixture is refluxed for 6 hours. The organic layer is again removed and washed with one liter of water. The washed product is dried by heating at 90° C. and 30 mm. Hg. pressure for 30 minutes. The residue is filtered through diatomaceous earth filter aid to give 2070 parts of a clear yellow-orange liquid.

EXAMPLE S-4

Into a reactor is charged 102.8 parts of sulfur chloride under a nitrogen atmosphere which is maintained throughout the reaction, and about 718.5 parts of gaseous isobutylene are fed into the reactor through a submerged line. The isobutylene is added as rapidly as possible while maintaining the maximum batch temperature at about 49° C. with a cooling water bath. After all of the isobutylene is added, the bath temperature decreases indicating completion of the reaction.

In a separate vessel, a mixture of 340.3 parts of an 18% sodium sulfide solution and 363.8 parts of a 50% aqueous solution of sodium hydroxide is prepared, and 128.77 parts of a 55.7% isopropyl alcohol and water mixture recovered from a previous batch are added. This addition is equivalent to 71 parts of dry isopropyl alcohol. The mixture is agitated, circulated and heated under reflux to a temperature of about 74° C. over a 2-hour period. While maintaining the batch temperature between about 75°-80° C., 168.13 parts of the isobutylene, sulfur chloride reaction product prepared above are added over a 5-hour period. The reaction mixture is maintained at about 80° C. and agitated for about 5 hours. The mixture then is cooled to about 38° C. and allowed to settle. The organic phase (138.7 parts) is separated from the aqueous phase and stripped of any remaining water and volatile materials. A filter aid is added to the residue with stirring, and the mixture then is filtered at about 50°-65° C. The filtrate is the desired product containing about 43% sulfur.

Reactant (C) The Catalyst

Reactant (C) is a catalytic amount of an amide of the structure $R_3CONR_4R_5$ wherein $R_3$, $R_4$ and $R_5$ are each independently hydrogen or a hydrocarbyl group containing from 1 to about 30 carbon atoms or an ethoxylated amide of the structure

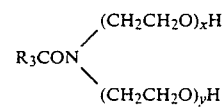

wherein the sum of x and y is from 1 to about 50. Preferably when $R_3$, $R_4$ and $R_5$ are hydrocarbyl groups, they contain from 1 to about 18 carbon atoms and most preferably from 1 to about 6 carbon atoms.

When $R_3$ is hydrogen and $R_4$ and $R_5$ are hydrocarbyl groups, Reactant (C) is a dihydrocarbyl formamide. Dihydrocarbylformamides having utility as a catalyst in this invention are: dimethylformamide, diethylformamide, dipropylformamide, methylethylformamide, dibutylformamide, methylbutylformamide, ethylbutylformamide, dioleylformamide, distearylformamide, didecylformamide, ditridecylformamide, decyltridecylformamide, decyloleylformamide, tridecyloleylformamide, etc.

When $R_3$ is a hydrocarbyl group and $R_4$ and $R_5$ are both hydrogen, Reactant (C) is a primary hydrocarbyl amide. Exemplary primary hydrocarbyl amides are acetamide, propionamide, butyramides, valeramide, lauramide, myristamide and palmitamide. The following simple fatty acid amides are available from Armak Company: coco fatty amide (Armid C), octadecanamide (Armid 18), hydrogenatedtallow fatty amide (Armid HT), oleamide (Armid O) and 13-docosenamide (Armid E).

When $R_3$ and $R_4$ are both hydrocarbyl groups and $R_5$ is hydrogen, Reactant (C) is an N-substituted amide. Exemplary N-substituted amides are N-methylacetamide, N-ethylacetamide, N-methylvaleramide, N-propyllauramide, N-methyloleamide and N-butylstearamide.

When $R_3$, $R_4$ and $R_5$ are all hydrocarbyl groups, Reactant (C) is an N,N-disubstituted amide. Exemplary N,N-disubstituted amides are N,N-dimethylacetamide, N-methyl-N-ethylacetamide, N,N-diethylpropionamide, N,N-dibutylvaleramide, N,N-diethylstearamide, N,N-dimethyloleamide.

Reactant (C) may also be an ethoxylated amide of the structure

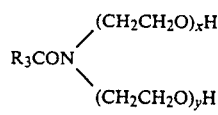

wherein the sum of x and y is from 1 to about 50, preferably 1 to about 20 and most preferably 1 to about 10.

The following table illustrates several of the many ethoxylated amides that may be utilized in the practice of this invention.

TABLE 1
Substituted Ethoxylated Fatty Acid Amides

| Chemical Identity | Trade name | Manufacturer |
|---|---|---|
| polyoxyethylated oleylamide $x + y = 5$ | Ethomid O/17 | Armak |
| RCON$<$(CH$_2$CH$_2$O)$_x$H / (CH$_2$CH$_2$O)$_y$H polyoxyethylated hydrogenated tallow fatty acid amide | | |
| $x + y = 5$ | Ethomid HT/15 | Armak |
| $x + y = 50$ | Ethomid HT/60 | Armak |
| N,N-bis(2-hydroxyethyl) dodecanamide | Ninol AA62 Extra | Stephen |
| N,N-bis(2-hydroxyethyl) coco fatty acid amide | Ninol 2021 Extra | Stephen |
| N,N-bis(2-hydroxyethyl) oleamide | EMID-6545 | Emery |
| N-2-hydroxyethyl cocamide | EMID-6500 | Emery |
| N-2-hydroxyethyl stearamide | EMID-6507 | Emery |

The compositions prepared by the method of this invention are formed by reacting the phosphite ester (A) with a sulfur source (B) in the presence of a catalytic amount of an amide (C). The molar ration of (A):(B) is at least from about 0.5:1 to about 5:1 and preferably 0.5:1 to about 2:1. (A) and (B) are reacted in the presence of (C) at a temperature from about ambient to about the decomposition temperature of any reactant or product. The molar ratio of (A):(C) is at least from about 1:0.01 to about 1:1; preferably from about 1:0.01 to about 1:0.5 and most preferably from about 1:0.01 to about 1:0.25.

Control Examples 1 and 2 are attempts to make dihydrocarbyl monothiophosphoric acids without the amide catalyst. Examples 1-3 employ an amide catalyst and are illustrative of the method of this invention.

CONTROL EXAMPLE 1

Charged to a 2-liter, 4-necked flask are 388 parts (2.00 moles) dibutyl phosphite and 64 parts (2.00 moles) sulfur. The contents are stirred and heated to 95° C. and held at this temperature for 3 hours. The contents are permitted to cool to room temperature overnight. Much unreacted sulfur is noted. The contents are filtered through a filter aid and the filtrate has the following analyses:

| | Found | Theory |
|---|---|---|
| % Phosphorus | 14.47 | 13.70 |
| % Sulfur | 9.0 | 14.16 |
| Acid number to phenolphthalein | 160 | 248 |

CONTROL EXAMPLE 2

Example 1 is repeated except that the contents are heated to 125° C. and held for 3 hours. The contents are permitted to cool to room temperature overnight and much unreacted sulfur is noted. The contents are filtered through a filter aid and the filtrate has the following analysis:

| | Found | Theory |
|---|---|---|
| % Phosphorus | 13.67 | 13.70 |
| % Sulfur | 11.70 | 14.16 |
| Acid number to phenolphthalein | 192 | 248 |

EXAMPLE 1

Charged to a 2-liter, 4-necked flask are 97 parts (0.50 moles) of dibutyl phosphite available from Mobil and 16 parts (0.50 moles) of sulfur. The reaction mixture is heated to 60° C. and 294 parts (0.50 moles) Ethomid 0/17 which is an oleyl amide reacted with 7 moles ethylene oxide, available from Akzo Chemie America are added in 0.5 hours. The temperature is raised to 95°-100° C. and held for 3 hours. The residue is filtered through a filter aid and the filtrate contains the desired dibutyl monothiophosphoric acid composition having the following analyses:

| | Found | Theory |
|---|---|---|
| % Nitrogen | 2.25 | 1.65 |
| % Sulfur | 3.73 | 3.93 |
| % Phosphorus | 3.31 | 3.81 |
| Acid number to phenolphthalein | 63.2 | 68.90 |

EXAMPLE 2

Charged to a 2-liter, 4-necked flask are 296 parts (0.50 moles) of dioleyl phosphite and 14.4 parts (0.45 moles) sulfur. The slurry is mixed while heating to 70° C. 142 parts (0.5 moles) of Armid O, an oleyl amide available from Armak, is added. The temperature is increased to 100° C. and held for 3 hours. The contents are filtered through a filter aid and the filtrate contains the desired dioleyl monothiophosphoric acid composition having the following analyses:

|  | Found | Theory |
|---|---|---|
| % Nitrogen | 1.67 | 1.55 |
| % Sulfur | 3.20 | 3.18 |
| % Phosphorus | 3.36 | 3.18 |
| Acid number to phenolphtalein bromophenol blue | 60.2 | 55.8 |

EXAMPLE 3

Charged to a 2-liter, 4-necked flask are 194 parts (1 mole) of dibutyl phosphite as employed in Example 3 and 28.8 parts (0.90 moles) of sulfur. The slurry is mixed and heated to 70° C. 283 parts (1.00 mole) of a mixture of oleylamide and linoleamide is added. The temperature is increased to 100° C. and held for 3 hours. The contents are filtered through a filter aid and the filtrate contains the desired dibutyl monothiophosphoric acid composition having the following analyses:

|  | Found | Theory |
|---|---|---|
| % Nitrogen | 2.81 | 2.76 |
| % Sulfur | 5.84 | 5.69 |
| % Phosphorus | 6.27 | 6.12 |
| Acid number to phenolphthalein | 95.80 | 99.80 |

EXAMPLE 4

Charged to a 2-liter, 4-necked flask are 194 parts (1.0 moles) of dibutyl phosphite and 32 parts (1.0 moles) of sulfur. The reaction mixture is heated to 90°-95° C. and 37 parts (0.1 moles) of Emid 6545 which is oleyl amide reacted with 2 moles of ethylene oxide, available from Emery, are added. The temperature is raised to 120° C. and held for 3 hours. The residue is filtered through a filter aid and the filtrate contains the desired dibutyl monothiophosphoric acid and composition having the following analyses:

|  | Found | Theory |
|---|---|---|
| % Nitrogen | 0.55 | 0.53 |
| % Sulfur | 11.01 | 12.17 |
| % Phosphorus | 9.93 | 11.79 |
| Acid number to phenolphthalein | 216 | 213 |

As previously indicated, the oil-soluble, dihydrocarbyl monothiophosphoric acid compositions of this invention are useful as additives for lubricants. They are particularly useful as oxidation inhibitors, corrosion inhibitors, rust inhibitors, and extreme pressure agents in gear and bearing lubricants. They can be employed in a variety of lubricants based on diverse oils of lubricating viscosity, including natural and synthetic lubricating and grease oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Also automatic transmission fluids, trans-axle lubricants, gear lubricants, metal-working lubricants, hydraulic fluids and other lubricating oil, grease compositions and aqueous systems can also benefit from the incorporation of the subject additive.

Natural oils include animal oils and vegetable oils (e.g., castor, lard oil), liquid petroleum oils and hydrorefined, solvent-treated or acid-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes)]; alkylbenzenes (e.g., dodecylbenzenes, tetradecylbenzenes, dinonylbenzenes, di(2-ethylhexyl) benzenes]] polyphenyls (e.g., biphenyls, terphenyls, alkylated polyphenyls); and alkylated diphenyl ethers and alkylated diphenyl sulfides and the derivatives, analogs and homologs thereof.

Alkylene oxide polymers and interpolymers and derivatives thereof where the terminal hydroxyl groups have been modified by esterification, etherification, etc., constitute another class known synthetic lubricating oils. These are exemplified by polyoxyalkylene polymers prepared by polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500); and mono- and polycarboxylic esters thereof, for example, the acetic acid esters, mixed $C_3$–$C_8$ fatty acid esters and $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol and tripentaerythritol.

Silicon-based oils such as the polyalkyl-, polyaryl-, polyalkoxy-, or polyaryloxysiloxane oils and silicate oils comprise another useful class of synthetic lubricants; they include tetraethyl silicate, tetraisopropyl silicate, tetra-(2-ethylhexyl) silicate, tetra-(4-methyl-2-ethylhexyl) silicate, tetra-(p-tertbutylphenyl) silicate, hexa-(4-methyl-2-pentoxy) disiloxane, poly(methyl)siloxanes and poly(methylphenyl) siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

Unrefined, refined and rerefined oils can be used in the lubricants of the present invention. Unrefined oils are those obtained directly from a natural or synthetic source without further purification treatment. For example, a shale oil obtained directly from retorting operations, a petroleum oil obtained directly from an esterification process and used without further treatment would be an unrefined oil. Refined oils are similar to the unrefined oils except that they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oil breakdown products.

Generally the lubricants of the present invention contain an amount of the oil-soluble, metal-containing compositions of this invention sufficient to inhibit oxidation, corrosion, rust and improve extreme pressure anti-wear properties. Normally the amount employed will be about 0.05% to about 20%, preferably about 0.1% to about 10% of the total weight of the lubricating composition. This amount is exclusive of any included solvent/diluent medium. In lubricating compositions operated under extremely adverse conditions, such as lubricating compositions for marine diesel engines, the metal salts of this invention may be present in amounts of up to about 30% by weight, or more, of the total weight of the lubricating composition.

The term "minor amount" as used in the specification and appended claims is intended to mean that when a composition contains a "minor amount" of a specific material that amount is less than 50 percent by weight of the composition.

The term "major amount" as used in the specification and appended claims is intended to mean that when a composition contains a "major amount" of a specific material that amount is more than 50 percent by weight of the composition.

The invention also contemplates the use of other additives in combination with the compositions of this invention. Such additives include, for example, detergents and dispersants of the ash-producing or ashless type, corrosion- and oxidation-inhibiting agents, pour point depressing agents, extreme pressure agents, antiwear agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-carbon phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with an excess of a metal neutralizing agent such as the metal oxide, hydroxide, carbonate, bicarbonate, or sulfide at a temperature about 50° C. The use of a "promoter" in the neutralization step to aid the incorporation of a large excess of metal likewise is known. Examples of compound useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenylnaphthylamine, and dodecylamine. A particularly effective method for preparing the salts comprises mixing an acid with an excess of a basic alkaline earth metal neutralizing agent and at least one alcohol promoter, and carbonating the mixture at an elevated temperature such as 60°-200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricant compositions of this invention. The following are illustrative:

(1) Reaction products of carboxylic acids (or derivatives thereof) containing at least about 34 and preferably at least about 54 atoms with nitrogen containing compounds such as amine, organic hydroxy compounds such as phenols and alcohols, and/or basic inorganic materials. Examples of these "carboxylic dispersants" are described in British Patent 1,306,529 and in many U.S. Pat. Nos. including the following:

| | | |
|---|---|---|
| 3,163,603 | 3,351,552 | 3,541,012 |
| 3,184,474 | 3,381,022 | 3,543,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | 4,234,435 |
| 3,346,493 | 3,522,179 | Re 26,433 |

(2) Reaction products of relatively high molecular weight aliphatic or alicyclic halides with amines, preferably polyalkylene polyamines. These may be characterized as "amine dispersants" and examples thereof are described for example, in the following U.S. Pat. Nos.: 3,275,554; 3,454,555; 3,438,757; and 3,565,804.

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. Pat. Nos. are illustrative:

| | | |
|---|---|---|
| 2,459,112 | 3,442,808 | 3,591,598 |
| 2,962,442 | 3,448,047 | 3,600,372 |
| 2,984,550 | 3,545,497 | 3,634,515 |
| 3,036,003 | 3,459,661 | 3,649,229 |
| 3,166,516 | 3,461,172 | 3,697,574 |
| 3,236,770 | 3,493,520 | 3,725,277 |
| 3,355,270 | 3,539,633 | 3,725,480 |
| 3,368,972 | 3,558,743 | 3,726,882 |
| 3,413,347 | 3,586,629 | 3,980,569 |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.:

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,422 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos.: 3,329,658; 3,366,730; 3,449,250; 3,687,849; 3,519,565 and 3,702,300. The above-noted patents are incorporated by reference herein for their disclosures of ashless dispersants.

Extreme pressure agents and corrosion- and oxidation-inhibiting agents which may be included in this invention are exemplified by chlorinated aliphatic hydrocarbons such as chlorinated wax; organic sulfides and polysulfides such as benzyl disulfide, bis(chlorobenzyl) disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 10 percent to 90 percent by weight of the composition of this invention and may contain, in addition, one or more other additives known in the art or described hereinabove.

Many of the above-mentioned extreme pressure agents and corrosion-oxidation inhibitors also serve as antiwear agents. Zinc dialkylphosphorodithioates are a well known example.

Pour point depressants are a particularly useful type of additive often included in the lubricating oils described herein. The use of such pour point depressants in oil-based compositions to improve low temperature properties is well known in the art. See, for example, page 8 of "Lubricant Additives" by C.V. Smalheer and R. Kennedy Smith (Lezius-Hiles Co. publishers, Cleveland, Ohio, 1967).

Examples of useful pour point depressants are polymethacrylates; polyacrylates; polyacrylamides; condensation products of haloparaffin waxes and aromatic compounds; vinyl carboxylate polymers; and terpolymers of dialkylfumarates, vinylesters of fatty acids and alkylvinylethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are hereby incorporated by reference for their relevant disclosures.

Anti-foam agents are used to reduce or prevent the formation of stable foam. Typical anti-foam agents include silicones or organic polymers. Additional anti-foam compositions are described in "Foam Control Agents", by Henry T. Kerner (Noyes Data Corporation, 1976), pages 125-162.

The oil-soluble compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 10 to 90% by weight of the oil-soluble compositions of this invention and may contain, in addition, one or more other additives known in the art or described hereinabove. The remainder of the concentrate is the substantially inert normally liquid diluent.

The fuel compositions of the present invention contain a major proportion of a normally liquid fuel, usually a hydrocarbonaceous petroleum distillate fuel such as motor gasoline as defined by ASTM Specification D-396. Normally liquid fuel compositions comprising nonhydrocarbonaceous materials such as alcohols, ethers, organonitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more nonhydrocarbonaceous materials are also contemplated. Examples of such mixtures are combinations of gasoline and ethanol, and diesel fuel and ether. Particularly preferred is gasoline, that is, a mixture of hydrocarbons having an ASTM boiling point of about 60° C. at the 10 percent distillation point to about 250° C. at the 90 percent distillation point.

Generally, these fuel compositions contain an amount of the composition of this invention sufficient to impart friction modification and/or deposit softening properties to the fuel; usually this amount is about 0.001 to about 5 percent (based on the weight of the final composition), preferably 0.001 percent to 1.0 percent.

The fuel compositions of this invention can contain, in addition to the compositions of this invention, other additives which are well known to those of skill in the art. These can include antiknock agents such as tetraalkyl lead compounds, lead scavengers such as haloalkanes (e.g., ethylene dichloride and ethylene dibromide), deposit preventers or modifiers such as triaryl phosphates, dyes, cetane improvers, auxiliary antioxidants such as 2,6-di-t-butyl-4-methylphenol, rust inhibitors such as alkylated succinic acids and anhydrides, bacteriostatic agents, gum inhibitors, metal deactivators, demulsifiers, upper cylinder lubricants, anti-icing agents and the like.

In certain preferred fuel compositions of the present invention, the aforedescribed compositions are combined with an ashless dispersant in gasoline. Such ashless dispersants are preferably esters of a mono- or polyol and a high molecular weight mono- or polycarboxylic acid acylating agent containing at least 30 carbon atoms in the acyl moiety. Such esters are well known to those of skill in the art. See, for example, French Patent No. 1,396,645, British Patent Nos. 981,850 and 1,055,337 and U.S. Pat. Nos. 3,255,108; 3,311,558; 3,331,776; 3,346,354; 3,522,179; 3,579,450; 3,542,680; 3,381,022; 3,639,242; 3,697,428; 3,708,522; and British Patent Specification 1,306,529. These patents are expressly incorporated herein by reference for their disclosure of suitable esters and methods for their preparation. Generally, the weight ratio of the compositions of this invention to the aforesaid ashless dispersants is about 0.1 to about 10.0, preferably about 1 to about 10 parts of compositions to 1 part ashless dispersant. In still another embodiment of this invention, the inventive additives are combined with Mannich condensation products formed from substituted phenols, aldehydes, polyamines, and substituted pyridines. Such condensation products are described in U.S. Pat. Nos. 3,649,659; 3,558,743; 3,539,633; 3,704,308; and 3,725,277.

The compositions of this invention can be added directly to the fuel to form the fuel compositions of this invention or they can be diluted with a substantially inert, normally liquid organic solvent/diluent such as mineral oil, xylene, or a normally liquid fuel as described above, to form an additive concentrate which is then added to the fuel in sufficient amounts to form the inventive fuel composition described herein. These concentrates generally contain about 10 to 90 percent of the compositions of this invention and can contain in addition any of the above described conventional dispersants in the aforesaid proportions. The remainder of the concentrate is the solvent/diluent.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of preparing a dihydrocarbyl monothiophosphoric acid composition represented by the formula

wherein $R_1$ and $R_2$ are each independently hydrocarbyl groups of from 1 to about 30 carbon atoms and X is oxygen or sulfur, with the proviso that one X is sulfur comprising reacting (A) a phosphite ester of the structure

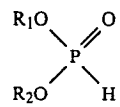

with (B) a sulfur source, in the presence of
(C) a catalytic amount of an amide of the structure $R_3CONR_4R_5$ wherein $R_3$, $R_4$ and $R_5$ are each independently hydrogen or a hydrocarbyl group containing from 1 to about 30 carbon atoms or an ethoxylated amide of the structure

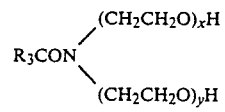

wherein the sum of x and y is from 1 to about 50.

2. The method of claim 1 wherein each of $R_1$ and $R_2$ are hydrocarbyl groups containing from about 4 to about 12 carbon atoms.

3. The method of claim 1 wherein the sulfur source is selected from the group consisting of elemental sulfur, a sulfur halide, sulfur dioxide, hydrogen sulfide and a sulfurized organic compound.

4. The method of claim 3 wherein the sulfur source is elemental sulfur.

5. The method of claim 1 wherein $R_3$ is hydrogen.

6. The method of claim 5 wherein $R_4$ and $R_5$ are hydrocarbyl groups containing from 1 to about 18 carbon atoms.

7. The method of claim 6 wherein $R_4$ and $R_5$ are hydrocarbyl groups containing from 1 to about 6 carbon atoms.

8. The method of claim 7 wherein $R_4$ and $R_5$ are methyl groups.

9. The method of claim 1 wherein $R_3$ is a hydrocarbyl group containing from 1 to about 18 carbon atoms and $R_4$ and $R_5$ are hydrogen.

10. The method of claim 9 wherein the amide is oleylamide.

11. The method of claim 1 wherein $R_3$ and $R_4$ are hydrocarbyl groups containing from 1 to about 18 carbon atoms and $R_5$ is hydrogen.

12. The method of claim 1 wherein $R_3$, $R_4$ and $R_5$ are hydrocarbyl groups containing from 1 to about 18 carbon atoms.

13. The method of claim 1 wherein the ethoxylated amide is polyoxyethylated oleylamide wherein the sum of x and y is 7.

14. The method of claim 1 wherein the molar ratio of (A):(B) is from about 0.5:1 to about 5:1.

15. The method of claim 1 wherein the molar ratio of (A):(B) is about 0.5:1 to about 2:1.

16. The method of claim 1 wherein the reaction of (A) and (B) in the presence of (C) is conducted at a temperature from about ambient to about the decomposition temperature of any reactant or product.

17. The method of claim 1 wherein the molar ratio of (A) to (C) is from about 1:0.01 to about 1:1.

18. The method of claim 1 wherein the molar ratio of (A) to (C) is from about 1:0.01 to about 1:0.5.

19. The method of claim 1 wherein the molar ratio of (A) to (C) is from about 1:0.01 to about 1:0.25.

* * * * *